United States Patent
Horbaschek

Patent Number: 5,630,414
Date of Patent: May 20, 1997

[54] X-RAY DIAGNOSTICS INSTALLATION FOR SUBTRACTION ANGIOGRAPHY

[75] Inventor: Heinz Horbaschek, Erlangen, Germany

[73] Assignee: Siemens Aktiengesellschaft, Munich, Germany

[21] Appl. No.: 405,871

[22] Filed: Mar. 17, 1995

[30] Foreign Application Priority Data

Apr. 18, 1994 [DE] Germany .......... 44 13 458.4

[51] Int. Cl.$^6$ ...................................... A61B 5/05
[52] U.S. Cl. .................. 128/653.1; 378/62; 378/63; 378/98.5
[58] Field of Search ............ 128/653.1; 378/62, 378/63, 8, 68, 69, 95, 98.5; 364/413.13, 413.14, 413.15

[56] References Cited

U.S. PATENT DOCUMENTS 4,433,428 2/1984 Haendle et al. .
4,709,385 11/1987 Pfeiler et al. .

FOREIGN PATENT DOCUMENTS 4133018 4/1993 Germany .
3520917 11/1993 Germany .

Primary Examiner—Marvin M. Lateef
Assistant Examiner—Brian L. Casler
Attorney, Agent, or Firm—Hill, Steadman & Simpson

[57] ABSTRACT

An X-ray diagnostics installation has an X-ray source and an X-ray image intensifier video chain, including an X-ray image intensifier, a video camera, a control circuit that derives control pulses for producing images of a subject from data supplied thereto identifying exposure conditions, and a subtraction circuit for forming the difference between stored video signals and continuing, current video signals given the same exposure conditions. The X-ray source is cyclically moved during the production of a number of successive images, with the control circuit deriving the control pulses for the production of images from apparatus positions and, possibly, from the ECG of the subject. The subtraction circuit forms the difference between predetermined video signals stored for different apparatus positions and heart phases of a heart cycle and continuing, current video signals obtained at the same apparatus positions and at the same heart phase.

10 Claims, 2 Drawing Sheets

5,630,414

X-RAY DIAGNOSTICS INSTALLATION FOR SUBTRACTION ANGIOGRAPHY

BACKGROUND OF THE INVENTION

1. Field of the Invention

The present invention is directed to an X-ray diagnostics installation of the type having an X-ray source, an X-ray image intensifier, a video camera, control means for generating control pulses for the acquisition of images, and subtraction means for forming the difference between stored video signals and continuous, current video signals under the same exposure conditions. Such X-ray diagnostics installations serve the purpose of marking vessels in a radiograph according to the so-called pathfinder technique.

2. Description of the Prior Art

European Application 0 193 712, corresponding to U.S. Pat. No. 4,709,385, discloses an X-ray diagnostics installation of the above general type, wherein images of a complete heart cycle are entered into an image memory as a mask scene under ECG control. The stored video signals of the vessel system belonging to the same heart phase can thereby be superimposed on the current video signal in fluoroscopic mode. Such an apparatus is utilized in the pathfinder technique.

This pathfinder technique is employed in cardiac angiography so that the examining person can recognize the course of a catheter after introduction thereof into the vessel paths, even without a contrast agent. To this end, the ongoing, dynamic fluoroscopic image that shows the catheter is superimposed with the vessel representation generated by subtraction angiography. As a result, the examining person recognizes the course of the vessels and can correspondingly control the catheter. A spatial recognizability of subtraction images in the fluoroscopic mode, however, is not possible.

It is known that an X-ray diagnostics installation of the above general type can produce displayed images having improved depth appearance by operation in a two-level or two-plane mode or using stereo irradiation of the subject. An undesirably high outlay, however, is necessary for this purpose since, for example, two X-ray systems must be employed given a two-plane mode. In an X-ray stereo apparatus disclosed in German PS 35 20 917, two X-ray sources arranged laterally next to one another are operated in alternation. The X-ray images are successively read into image memories, so that an X-ray stereo pair is contained therein, this pair being supplied to the respective eyes of an observer via two separate monitors. Increased outlay occurs as a result of the stereo reproduction means and, moreover, the observation means required, for example polarization eyeglasses, limit the field of vision of the examining person.

SUMMARY OF THE INVENTION

An object of the present invention is to provide an X-ray diagnostics installation of the general type initially described which achieves improved spatial (depth) appearance in the pathfinder technique without added apparatus outlay, even in the case of examinations in the area of the skull.

This object is inventively achieved in an X-ray diagnostics installation of the above general type which further includes drive means for relatively adjusting a patient bed and the X-ray source so that a cyclical relative adjustment into a plurality of exposure positions is conducted during the production of a like plurality of successive images. A detector is provided for acquiring the exposure positions that is connected to the control means, with the control means deriving control pulses therefrom for the production of the images from the exposure positions. The subtraction means is fashioned such that it forms the differences between predetermined video signals stored for different exposure positions and continuous, current video signals given the same exposure positions. This results in the stored video signal of the vessel system belonging to the same apparatus position or exposure position being superimposed on the current video signal for that apparatus or exposure in the fluoroscopic mode (for example, in general anglo- or neuroradiology), causing a pseudo-3D image impression to the viewer due to the motion. Spatial visibility is thereby improved, especially given examinations in the area of the skull.

The apparatus of the invention can also be advantageously utilized in cardioangiography in an embodiment wherein, in the manner discussed above, the control means derives the control pulses for the production of images from the ECG of the patient and the subtraction inventively comprises means for forming the difference between video signals stored for different apparatus positions and heart phases of a heart cycle and continuing, current video signals of the same apparatus position and same heart phase.

In an X-ray diagnostics installation of the type having a carrying arm for holding the X-ray radiator and the X-ray image intensifier, it has proven advantageous for the carrying arm with the X-ray radiator and the X-ray image intensifier to be moved in order to produce the aforementioned relative positioning. Another inventive embodiment of an X-ray diagnostics installation is obtained when the X-ray source is displaced or turned around a center axis.

It has proven advantageous, when a sequence of a plurality of X-ray images is registered as the stored video signal, for at least one motion cycle to be implemented during the registration. Inventively, the registrations can also ensue in only two positions.

Jittery X-ray images that occur because of images being obtained at too few positions can be avoided when the subtraction means is fashioned such that it interpolates successive images for producing intermediate images.

DESCRIPTION OF THE PREFERRED EMBODIMENTS

Figure 1:
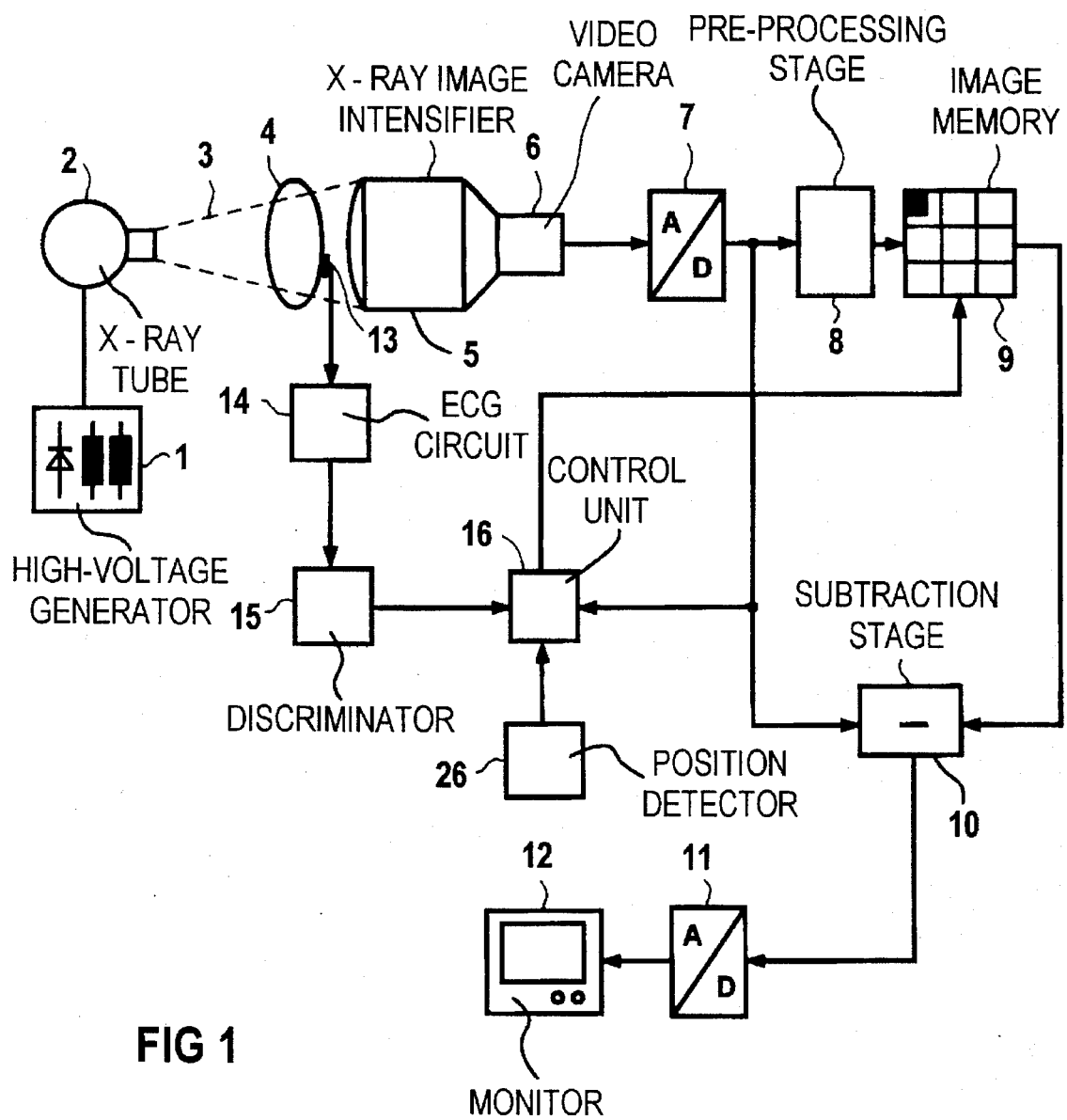
FIG. 1 is a circuit arrangement of an X-ray diagnostics installation constructed in accordance with the principles of the present invention.

FIG. 1 shows an X-ray diagnostics installation of the invention having a high-voltage generator 1 that feeds an X-ray tube 2 as the X-ray source. The X-ray tube 2 emits X-rays in a beam path 3 in which a patient 4, who has been; or will be, injected with contrast agent, is disposed. An X-ray image intensifier 5 following in the beam path 3 is coupled to a video camera 6 whose output signal is supplied to an analog-to-digital (A/D) converter 7. The digitized video signal is read into an image memory 9 via a preprocessing stage 8, which can determine when the maximum contrast agent flow (concentration) occurs, with or without integration. The image memory 9 has a storage capacity of several individual frames. The output of the image memory 9 is connected to one input of a subtraction stage 10 to whose second input the A/D converter 7 is connected. The output signal of the subtraction stage 10 is supplied to a digital-to-analog (D/A) converter 11 whose analog output signal is shown in a monitor 12.

ECG electrodes 13 are applied to the patient 4, these electrodes being connected to an ECG circuit 14. The ECG signal of the ECG circuit 14 is supplied to a discriminator 15 for the amplitude and phase of the ECG signal. The discriminator 15 is connected to a control unit 16 that controls the entry of the frames into the image memory 9. The ECG circuit 14, the discriminator 15 and the control unit 16 form an exposure control means that, for example, can be constructed as described in German OS 31 24 583, corresponding to U.S. Pat. No. 4,433,428.

In the fluoroscopic mode, the digital video signals at the output of the A/D converter 7 are read into a storage location of the image memory 9 over at least one heart cycle as an auxiliary mask. Subsequently, the patient is injected with a contrast agent. The entry of the fluoroscopic images into the image memory 9 is triggered at the maximum of the contrast agent concentration, whereupon the storage location for the auxiliary mask can be overwritten since this is no longer required. After the appearance of a recognition feature of the ECG, for example the R-wave, the exposures belonging to different heart phases of a heart cycle are successively written as a mask cycle. After the conclusion of the exposure entry, the individual frames contained in the image memory 9 are read out synchronized, with respect to the heart phase, with the current video signal. As a result, the vessel system appears on the monitor 12 as a bright or light image superimposed on the rest of the image content. A catheter can now be introduced into and correctly guided in the vessels made visible in this way. As a result of the read-out of the image memory 9 heart phase synchronized with the current video signal, individual frames that correspond to one another are subtracted, so that it is assured in every instance that the vessels derived from the stored image correspond to the real contours.

Figure 2:
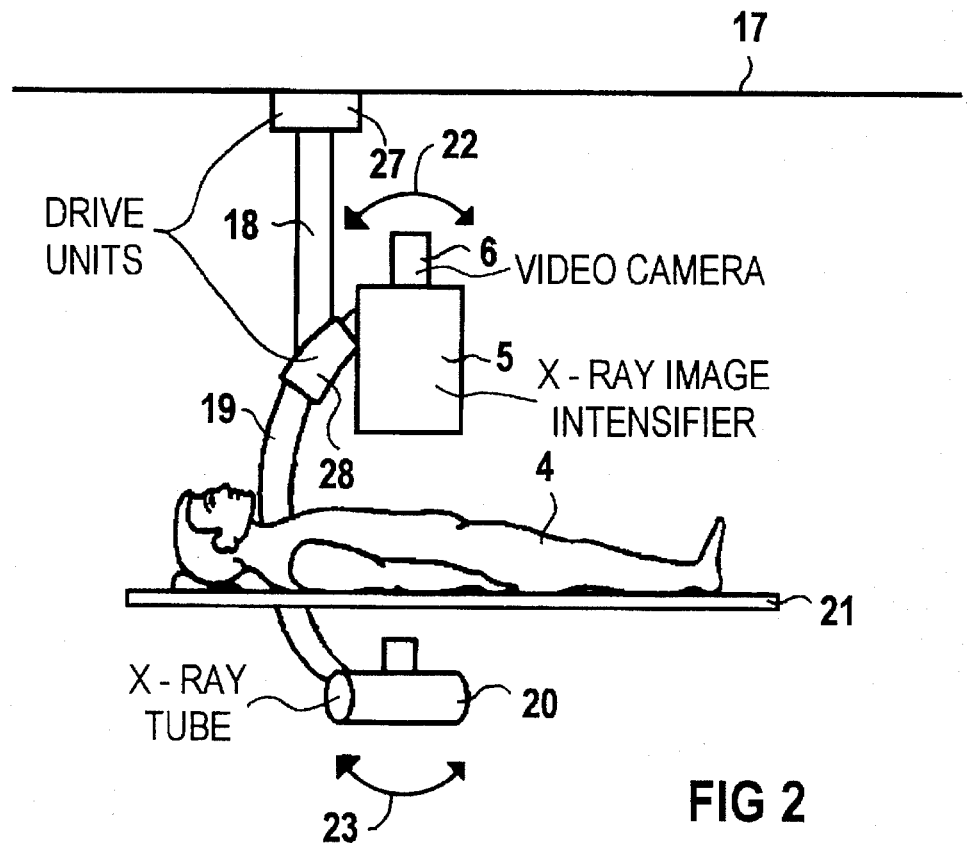
FIG. 2 shows the mechanical structure of the X-ray diagnostics installation of the invention shown in FIG. 1.

FIG. 2 shows an X-ray diagnostics installation of the invention that can include the aforementioned electrical structure of FIG. 1. This X-ray diagnostics installation has a movable holder 18 attached, for example, to the ceiling 17 via a drive unit 27 for moving the holder 18. The holder 18 holds a C-arm which can be rotated by a drive unit 28. An X-ray radiator 20, containing an X-ray tube 2 as the X-ray source, and, disposed opposite thereto, an X-ray image intensifier 5 coupled to a video camera 6 or some other X-ray detector, are attached to the respective ends of the C-arm 19. A patient bed 21 with a patient 4 can be introduced into the beam path of the X-ray radiator 20. For example, the C-arm 19 can be rotated around a pivot point by the drive unit 28, so that both the image intensifier 5, video camera unit 6 and the X-ray radiator 20 can be rotated around a common pivot point in the direction of the arrows 22 and 23. This rotation ensues cyclically with a speed of, for example, 2 seconds per cycle, so that an excessive instability of the images does not occur. Parallel displacements of the image are entirely or partially compensated by a displacement correction as in the case of stereo mode.

Instead of rotating the C-arm 19, the motion of the X-ray source 2 can be achieved in all other directions of motion permitted by the overall X-ray diagnostics installation. Thus, for example, the patient bed 21 with the patient 4 or the movable holder 18 with the C-arm 19 attached to the ceiling 17 can also be moved by the drive unit 27. A displacement of only the focus of the X-ray tube 2 as described in U.S. Pat. No. 5,313,510, or of only the X-ray radiator 20, is also possible.

Inventively, a position detector 26 shown in FIG. 1 is connected to the control unit 16. The position detector 26 recognizes the motion of the X-ray apparatus, or recognizes an apparatus position or focus position and supplies a signal to the control unit 16, so that exposures of a mask cycle are stored for every exposure position.

Figures 3, 4, 5, 6, 7:
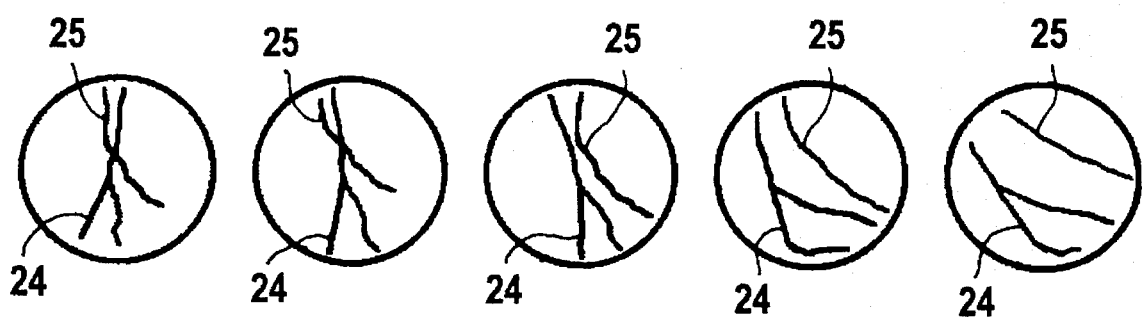
FIGS. 3 through 7 show respective fluoroscopic images from different radiation angles obtained using the inventive installation.

Two rotated images thus arise, the tip of the catheter, for example, lying in the pivot point (the center). Such fluoroscopic images are shown in FIGS. 3 through 7. In FIG. 3, the vessels 24 and 25 are shown in their initial position at 0°. By rotating the C-arm 19 by the drive unit 28 in the direction of the arrows 22 and 23, for example, into a position of 2.5°, the positions of the vessels 24 and 25 shown in FIG. 4 are obtained for this exposure position. FIGS. 5 through 7 show the respective fluoroscopic images with the pathfinder technique for exposure positions of, for example, 5°, 7.5° and 10°. A pseudo-3D image that enables limited three-dimensional vision is produced by this cyclical motion of the C-arm 19 with the X-ray radiator 20 and image intensifier 5 as well as the video camera 6. Utilized in pathfinder technique, this means that two motion cycles are required for producing a subtraction mask in order to subsequently implement the fluoroscopy with further motion cycles synchronized with the mask images.

The mask cycle can be eliminated if a preceding, matching image acquisition is undertaken, for example an image obtained using digital subtraction angiography (DSA) having an apparatus motion, preceding, for example, an image obtained using rotation angiography and without apparatus motion.

In order to avoid jittery images, interpolation of successive images can ensue to form intermediate images, so that X-ray images having exposure angles that lie between the actual exposure angles can be produced electronically.

The gantry can also be displaced by means of a soft or gliding motion, and triggering of the exposures ensues proceeding from the apparatus position.

For correcting registration errors, a device that implements an automatic pixel shift is utilized, so that small differences in position are compensated, or an exact rotation is achieved, based on reference subjects in the image.

As a further alternative, it is possible to move the X-ray system only for the production of fill images.

The position of the X-ray system can be adjusted during the pathfinder fluoroscopy during the manipulation, so that the observation angle can be modified manually as needed.

Control of the X-ray system can ensue on the basis of an automatic follow-up with head or eye movements being acquired and utilized for control.

The movement of the focus can also be achieved in some other fashion. For example, the overall X-ray apparatus can be shifted, or a focus shifting of only the X-ray tube 2 can ensue.

Although various minor modifications may be suggested by those versed in the art, it should be understood that I wish to embody within the scope of the patent granted hereon all such modifications as reasonably and properly come within the scope of my contribution to the art.

I claim as my invention:

1. An X-ray diagnostics installation comprising:

a subject support;

an X-ray source which emits an X-ray beam;

an X-ray image intensifier for detecting X-rays in said X-ray beam emitted by said X-ray source and attenuated by a subject to produce X-ray images;

video processing means, including a display, for generating video images from said X-ray image and for displaying said video images on said display;

drive means for cyclically producing relative movement between said subject support and said X-ray beam for producing a plurality of cycles of identical exposure positions;

detector means for generating a detector signal identifying when each of said exposure positions is reached;

control means for controlling said video processing means for producing an X-ray image and a video image of said subject at each of said exposure positions;

memory means for storing a plurality of video images, as stored video images, respectively produced at a plurality of different exposure positions in a cycle; and subtraction means, in said video processing means, for forming a series of difference images respectively from said stored video images and a plurality of current video images respectively obtained during a current cycle at the same exposure positions as said stored video images, said difference images being displayed on said display.

2. An X-ray diagnostics installation as claimed in claim 1, further comprising means for obtaining an electrocardiographic signal from said subject, said electrocardiographic signal including signal characteristics respectively identifying phases of a cardiac cycle, wherein said memory means comprises means for storing video phase images, as said stored video images, obtained at respectively different exposure positions and phases of a cardiac cycle, and wherein said subtraction means comprises means for forming said series of difference images from the video phase images stored in said memory means and current video phase images obtained at the same exposure position and at the same phase of the cardiac cycle as the video phase images stored in said memory means.

3. An X-ray diagnostics installation as claimed in claim 1, wherein said drive means comprises means for moving said X-ray source.

4. An X-ray diagnostics installation as claimed in claim 1, wherein said X-ray source has a focus from which said X-ray beam emanates and wherein said drive means comprises means for moving said focus.

5. An X-ray diagnostics installation as claimed in claim 1, further comprising an X-ray radiator containing said X-ray source, a carrying arm on which said X-ray radiator and said X-ray image intensifier are mounted, and wherein said drive means comprises means for moving said X-ray radiator and said X-ray image intensifier by moving said carrier arm.

6. An X-ray diagnostics installation as claimed in claim 5, wherein said drive means comprises means for displacing said X-ray source.

7. An X-ray diagnostics installation as claimed in claim 5, wherein said carrier arm is curved and has a center, and wherein said drive means comprises means for moving said carrier arm to rotate said X-ray source around said center.

8. An X-ray diagnostics installation as claimed in claim 1, wherein said control means comprises means for producing two X-ray images and two corresponding video images at each exposure position with said X-ray source respectively rotated at a different angle for each of said two X-ray and video images.

9. An X-ray diagnostics installation as claimed in claim 8, wherein said memory means comprises means for storing said video images produced during at least one cycle.

10. An X-ray diagnostics installation as claimed in claim 1, wherein said subtraction means comprises means for interpolating successive images of said stored video images and said current video images for generating intermediate difference images, said intermediate difference images being displayed on said display between respective difference images.

* * * * *